(12) United States Patent
Baumgart (10) Patent No.: US 8,848,996 B2
(45) Date of Patent: Sep. 30, 2014

(54) SYSTEM FOR SUPPRESSING VASCULAR STRUCTURE IN MEDICAL IMAGES

(71) Applicant: John Baumgart, Hoffman Estates, IL (US)

(72) Inventor: John Baumgart, Hoffman Estates, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 101 days.

(21) Appl. No.: 13/747,708

(22) Filed: Jan. 23, 2013

(65) Prior Publication Data

US 2013/0216119 A1 Aug. 22, 2013

Related U.S. Application Data

(60) Provisional application No. 61/599,967, filed on Feb. 17, 2012.

(51) Int. Cl.
| | |
|---|---|
| *G06K 9/00* | (2006.01) |
| *A61B 5/145* | (2006.01) |
| *A61B 6/00* | (2006.01) |
| *G06T 5/50* | (2006.01) |

(52) U.S. Cl.
CPC . *A61B 5/14* (2013.01); *A61B 6/504* (2013.01); *G06T 2207/20224* (2013.01); *G06T 2207/30101* (2013.01); *G06T 2207/10116* (2013.01); *A61B 6/4441* (2013.01); *G06T 2207/20148* (2013.01); *A61B 6/5235* (2013.01); *A61B 6/481* (2013.01); *A61B 6/5258* (2013.01); *G06T 5/50* (2013.01); *Y10S 128/922* (2013.01)
USPC ............................. 382/130; 128/922; 378/4

(58) Field of Classification Search
USPC ............... 382/100, 128, 129, 130, 131, 132; 128/922; 378/4–27
See application file for complete search history.

(56) References Cited

U.S. PATENT DOCUMENTS

| | | | | |
|---|---|---|---|---|
| 6,134,353 | A * | 10/2000 | Makram-Ebeid | 382/259 |
| 6,493,569 | B2 * | 12/2002 | Foo et al. | 600/410 |
| 7,369,691 | B2 * | 5/2008 | Kondo et al. | 382/128 |
| 7,783,092 | B2 * | 8/2010 | Agam et al. | 382/128 |
| 7,912,269 | B2 * | 3/2011 | Ikeda et al. | 382/131 |
| 8,275,449 | B2 * | 9/2012 | White et al. | 600/431 |
| 8,417,319 | B2 * | 4/2013 | Mallya et al. | 600/425 |
| 8,509,507 | B2 * | 8/2013 | Meetz et al. | 382/128 |
| 2007/0165921 | A1 * | 7/2007 | Agam et al. | 382/128 |
| 2010/0104168 | A1 * | 4/2010 | Dobbe | 382/134 |
| 2011/0001761 | A1 * | 1/2011 | Sakuragi | 345/634 |
| 2012/0150048 | A1 * | 6/2012 | Kang et al. | 600/481 |
| 2012/0236259 | A1 * | 9/2012 | Abramoff et al. | 351/206 |
| 2013/0294672 | A1 * | 11/2013 | Meetz et al. | 382/131 |

* cited by examiner

*Primary Examiner* — Anand Bhatnagar
(74) *Attorney, Agent, or Firm* — Brennan K Bradley (57) ABSTRACT

A system generates medical image data representing smaller vessels including capillaries of a region of patient anatomy. An image data processor identifies pixels of larger vessels in individual images of difference images where the larger vessels have a size exceeding a predetermined threshold size. The image data processor generates an enhanced visualization small vessel image comprising substantially peak luminance values of individual pixels exclusive of pixels of the identified larger vessels. A peak luminance value of an individual pixel is generated in response to a peak luminance value of luminance values of pixels, spatially corresponding to the individual pixel and present in images comprising the plurality of temporally sequential individual difference images. An output processor outputs substantially peak luminance values as a vessel image.

16 Claims, 6 Drawing Sheets

SYSTEM FOR SUPPRESSING VASCULAR STRUCTURE IN MEDICAL IMAGES

This is a non-provisional application of provisional application Ser. No. 61/599,967 filed Feb. 17, 2012, by J. Baumgart.

FIELD OF THE INVENTION

This invention concerns a system for generating an enhanced visualization small vessel medical image representing smaller vessels including capillaries of a region of patient anatomy using substantially peak pixel luminance values.

BACKGROUND OF THE INVENTION

In known subtracted angiographic x-ray image acquisition, an object of interest is typically patient vasculature. There are instances, however, where perfusion of contrast agent through capillaries is of interest. Unfortunately, such capillary perfusion is not easily visualized due to both faint appearance of the capillaries relative to larger vessels and the capillaries being obscured by the larger vessels in an image. A system according to invention principles addresses these deficiencies and related problems.

SUMMARY OF THE INVENTION

A system suppresses vascular structure in X-ray images improving visualization of capillary blush phases of a contrast agent injection, particularly during use of substantially maximum opacification to visualize peak contrast over an area over time. A system generates medical image data representing smaller vessels including capillaries of a region of patient anatomy. At least one repository stores data representing multiple temporally sequential individual difference images of vessels of a region of interest of patient anatomy derived by subtracting data representing a first mask image acquired in the absence of contrast agent from individual images of temporally sequential individual images acquired in the presence of contrast agent. An image data processor identifies pixels of larger vessels in individual images of the difference images where the larger vessels have a size exceeding a predetermined threshold size. The image data processor generates an enhanced visualization small vessel image comprising substantially peak luminance values of individual pixels exclusive of pixels of the identified larger vessels. A peak luminance value of an individual pixel is generated in response to a peak luminance value of luminance values of pixels, spatially corresponding to the individual pixel and present in images comprising the plurality of temporally sequential individual difference images. An output processor provides the substantially peak luminance values representing the enhanced visualization small vessel image to a destination.

DETAILED DESCRIPTION OF THE INVENTION

A system generates a maximally perfused image in which individual image picture elements (pixels) represent peak (substantially maximally opacified) contrast agent at their respective image locations in multiple images acquired over the duration of contrast agent flow. In the case of a maximally perfused image however, the vessel structure is advantageously removed from each image prior to processing for inclusion into a substantially maximally opacified resultant image. The resultant image advantageously provides enhanced visualization of capillary (or parenchymal) perfusion.

Figure 1:
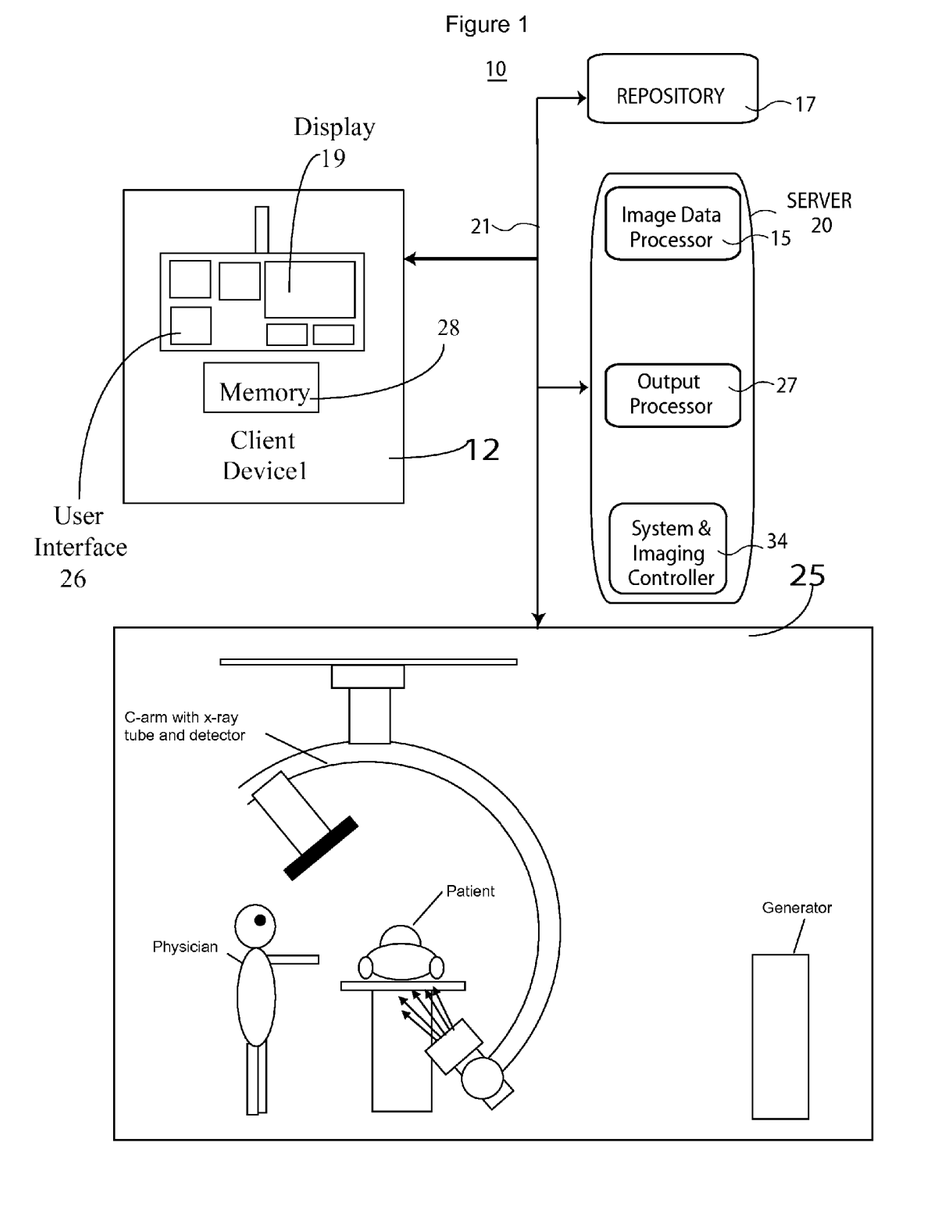
FIG. 1 shows a system for generating medical image data representing smaller vessels including capillaries of a region of patient anatomy, according to invention principles.

FIG. 1 shows system 10 for generating medical image data representing smaller vessels including capillaries of a region of patient anatomy. System 10 includes one or more processing devices (e.g., workstations, computers or portable devices such as notebooks, Personal Digital Assistants, phones) 12 that individually include memory 28, a user interface 26 enabling user interaction with a Graphical User Interface (GUI) and display 19 supporting GUI and medical image presentation in response to predetermined user (e.g., physician) specific preferences. System 10 also includes at least one repository 17, server 20, and imaging device 25. Server 20 includes image data processor 15, output processor 27 and system and imaging control unit 34. System and imaging control unit 34 controls operation of one or more imaging devices 25 for performing image acquisition of patient anatomy in response to user command. Imaging devices 25 may comprise a mono-plane or biplane X-ray imaging system. The units of system 10 intercommunicate via network 21. At least one repository 17 stores X-ray medical images and studies for patients in DICOM compatible (or other) data format. A medical image study individually includes multiple image series of a patient anatomical portion which in turn individually include multiple images. At least one repository 17 stores data representing multiple temporally sequential individual difference images of vessels of a region of interest of patient anatomy derived by subtracting data representing a first mask image acquired in the absence of contrast agent from individual images of temporally sequential individual images acquired in the presence of contrast agent.

Image data processor 15 identifies pixels of larger vessels in individual images of multiple difference images. The larger vessels have a size exceeding a predetermined threshold size. Processor 15 generates an enhanced visualization small vessel image comprising substantially peak luminance values of individual pixels exclusive of pixels of the identified larger vessels. A peak luminance value of an individual pixel is generated in response to a peak luminance value of luminance values of pixels, spatially corresponding to the individual pixel and present in images comprising the multiple temporally sequential individual difference images. Output processor 27 provides the substantially peak luminance values representing the enhanced visualization small vessel image to a destination.

Figure 2:
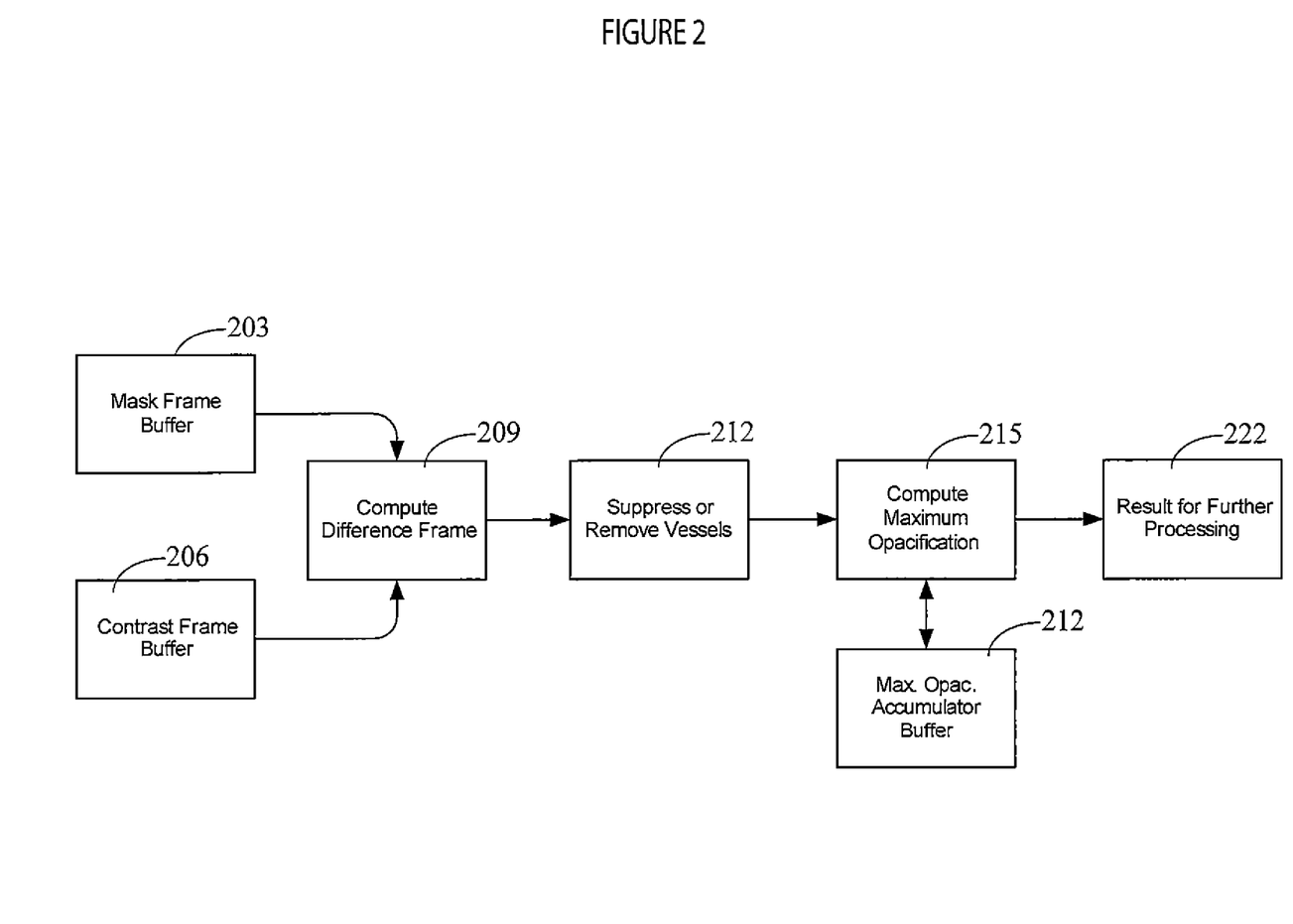
FIG. 2 shows a system for constructing a maximally perfused image from an angiographic x-ray image sequence acquisition using image data subtraction, according to invention principles.

FIG. 2 shows a system for constructing a maximally perfused image from an angiographic x-ray image sequence acquisition using image data subtraction. Image data processor 15 (FIG. 1) in step 209 derives data representing an individual difference image, S, of vessels of a region of interest of patient anatomy by subtracting data representing a first mask image from buffer 203 acquired in the absence of contrast agent, from an image from buffer 206 acquired in the presence of contrast agent. Difference image S comprises an image frame of vasculature without contrast agent (first mask) subtracted from an image frame of the corresponding vasculature containing contrast agent. This is termed digital subtraction angiography (DSA). Digital subtraction angiography or DSA is an imaging method used for visualizing blood vessels inside a patient's body that includes injecting a contrast agent bolus, that is substantially opaque to X-rays, into the blood vessels or vasculature under study as images are acquired by the X-ray diagnostic imaging system. Prior to acquisition of the contrast image, a mask image without contrast is acquired. A difference image is calculated by superimposing upon and subtracting the mask image from the contrast image. Ideally, nothing appears in the difference image other than the image of the blood vessels.

In step 212 vessels are suppressed and removed to create a second mask image from the difference image S. The second mask image indicates pixels from the difference frame that are to be excluded from a maximum opacification image. In one embodiment, processor 15 suppresses and removes vessels to create a second mask from the difference frame, S. The second mask comprises pixels from the difference frame S that are not to be introduced into a maximum opacification image. Processor 15 generates the second mask image by filtering difference image frame S with a band-pass filter that preserves structures that are the size of the vessels that are to be removed. For a typical 1024×1024 pixel resolution input image, in one embodiment the bandpass filter preserves structures from 3 to 40 pixels wide. In another embodiment, the bandpass filter preserves a different range of structure size based on the physical size of the object being removed and the resolution of the image being used.

The resultant band-pass filtered image data is compared to a threshold to generate a threshold image $I_T$, where $I_T(x,y)=1$ if the gray level of the band-pass image is greater than the threshold, and of 0 value if not. The pixels of $I_T$ that are of value 1 correspond to vessel pixels and form the second mask used to exclude difference image pixels from opacification. Processor 15 configures the threshold to be a specific gray value or automatically selects the threshold based on a histogram analysis of an image showing a significant amount of contrast agent filled vasculature to separate the vessels from the background. Luminance values of pixels of the band-pass filtered resultant image data exceeding the threshold indicate vessel pixels used to form the second mask. The second mask is used to exclude difference image pixels in step 212 from a substantially maximally opacified image.

In forming a maximally opacified image in step 215, an image in a maximum opacification buffer 218 is processed using the second mask image to exclude pixels identified in the second mask from the maximally opacified image in forming a new image comprising an enhanced visualization small vessel image. The new image comprises peak luminance values of individual pixels exclusive of pixels of the identified larger vessels. The image in maximum opacification buffer 218 comprises peak luminance values of individual pixels in each of the component images of a sequence of images where each pixel represents the most opacified pixel value at a particular pixel location. A peak luminance value of an individual pixel is selected from luminance values of pixels, spatially corresponding to the individual pixel in the sequence of images. The new image is output in step 222 for further processing.

Figure 3:
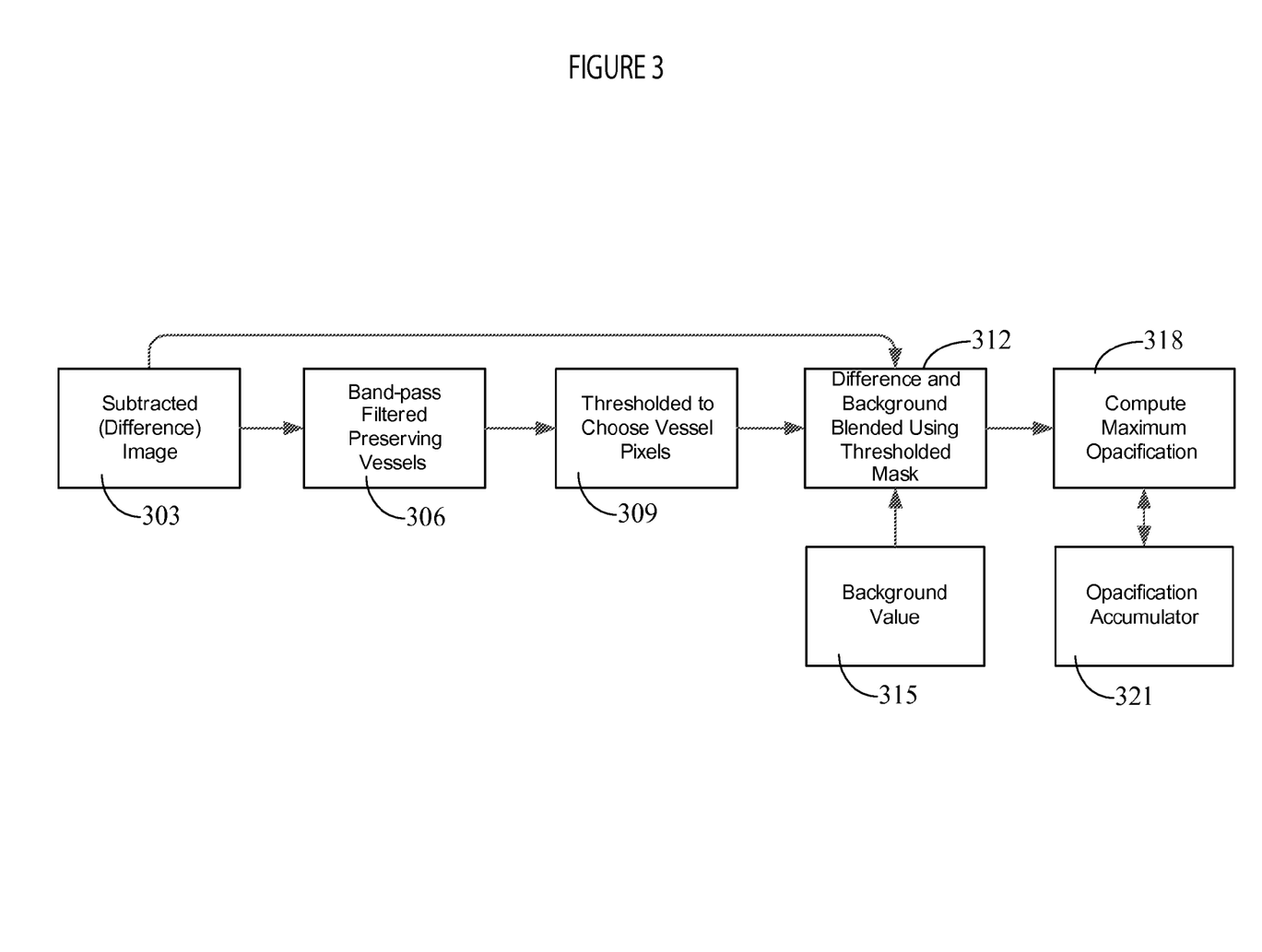
FIG. 3 shows a process for band-pass filtering difference pixel values to preserve structures that are the size of the vessels that are to be removed, according to invention principles.

FIG. 3 shows a process employed by system 10 (FIG. 1) for band-pass filtering difference pixel values to preserve structures that are the size of the vessels that are to be removed. In this embodiment, the second mask is derived by partially incorporating difference pixel values. Difference frame S 303 is band-pass filtered in step 306 preserving structures that are the size of the vessels that are to be removed. The resultant band-pass filtered image data is compared to a threshold in step 309 to generate a threshold image used to emphasize luminance of a vessel and each vessel pixel, enabling vessel edges to be faded out for a more natural look. The vessel luminance intensity is used in step 312 as an alpha-blending factor in blending a filtered difference image derived in step 309 and a neutral background 315. In addition to being used directly as the mask for blending the difference frame S and the background B, the threshold image derived in step 309 is used to derive a different mask for this purpose. Operations performed by processor 15 on the threshold image used to generate this mask include, blurring the mask to soften the edges of the vessels, enlarging or reducing the areas shown to be vessels and connecting adjacent vessel segments.

Second mask image pixel values, M derived in step 309 are used as a series of alphablending values to combine subtracted image, S 303, with the background, B 315, to provide the luminance for each pixel in step 312 in an output image, Ip, where, $$I_P(x,y)=S(x,y)M(x,y)+B(x,y)(1-M(x,y))$$

The resultant band-pass filtered blended image data is compared to a threshold in step 312 to generate a threshold image $I_p$, where $I_p(x,y)=1$ if the gray level of a blended image pixel is greater than or equal to the threshold, and $I_p(x,y)=0$ if the gray level of the blended image pixel is less than the threshold. Luminance values of pixels of the band-pass filtered blended thresholded resultant image data exceeding the threshold indicate vessel pixels used to form the second mask. The second mask is used to exclude difference image pixels in step 318 from a substantially maximally opacified image.

In forming a maximally opacified image in step 318, an image in a maximum opacification buffer 321 is processed using the second mask image to exclude pixels identified in the second mask from the maximally opacified image in forming a new image comprising an enhanced visualization small vessel image. The new image comprises peak luminance values of individual pixels exclusive of pixels of the identified larger vessels. The image in maximum opacification buffer 321 comprises peak luminance values of individual pixels in each of the component images of a sequence of images where each pixel represents the most opacified pixel value at a particular pixel location. A peak luminance value of an individual pixel is selected from luminance values of pixels, spatially corresponding to the individual pixel in the sequence of images. In one embodiment, the term "peak luminance" is used to indicate maximum opacification. While this may be true for radiography, for angiography, peak luminance may comprise minimum opacification and the darkest pixels that represent the maximal opacification. This constraint is not necessary, however, as an image can be inverted so that peak luminance is maximum opacification.

Figure 4:
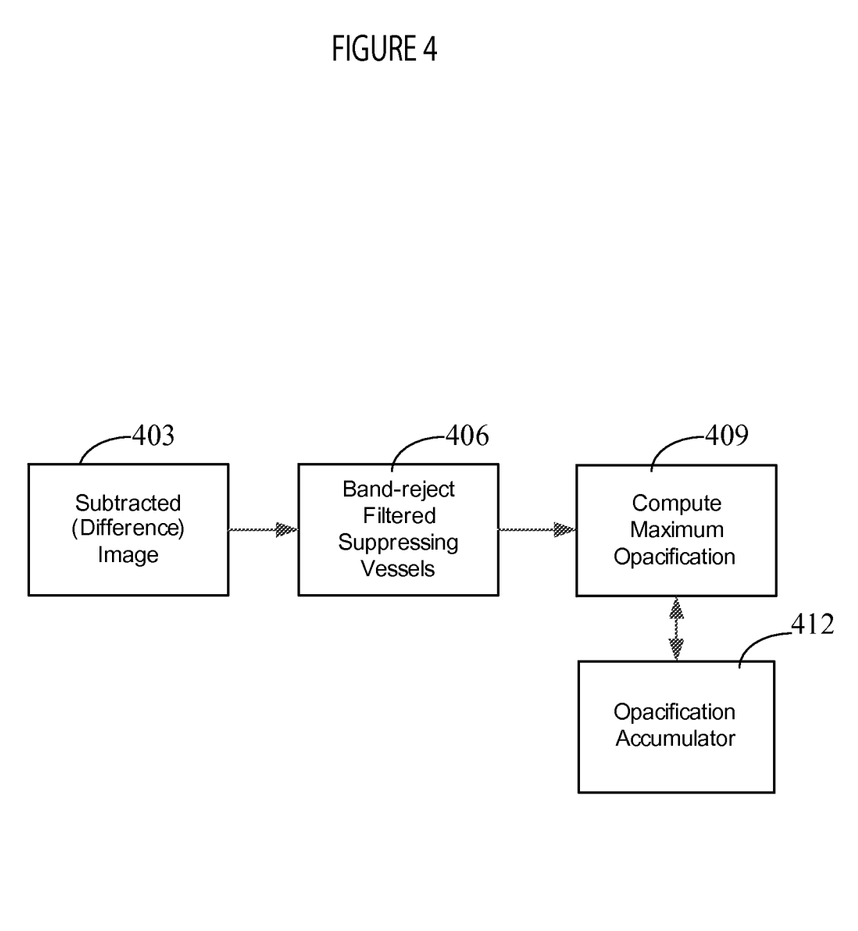
FIG. 4 shows a process for filtering a difference image with a band-reject filter to filters out structures that are the size of vessels thereby suppressing the vessel structures, according to invention principles.

FIG. 4 shows a process employed by system 10 (FIG. 1) for filtering a difference image with a band-reject filter to filter out structures that are the size of vessels thereby suppressing the vessel structures. In this embodiment, processor 15 filters a difference image with a band-reject filter, which filters out structures that are the size of vessels thereby suppressing the vessel structures. The output of the band-reject filter is used directly in accumulation of a maximally opacified image. Difference frame S 403 is band-reject filtered in step 406 suppressing structures that are the size of the vessels that are to be removed. The resultant band-reject filtered image data is used in selecting image pixels in step 409 of a maximally opacified image. In forming a maximally opacified image in step 409, an image in a maximum opacification buffer 412 is processed using the resultant band-reject filtered image data to include the filtered pixels but to exclude pixels of the suppressed structures that are the size of the vessels that are to be removed. The image in maximum opacification buffer 412 comprises peak luminance values of individual pixels in each of the component images of a sequence of images where each pixel represents the most opacified pixel value at a particular pixel location. A peak luminance value of an individual pixel is selected from luminance values of pixels, spatially corresponding to the individual pixel in the sequence of images.

Figure 5:
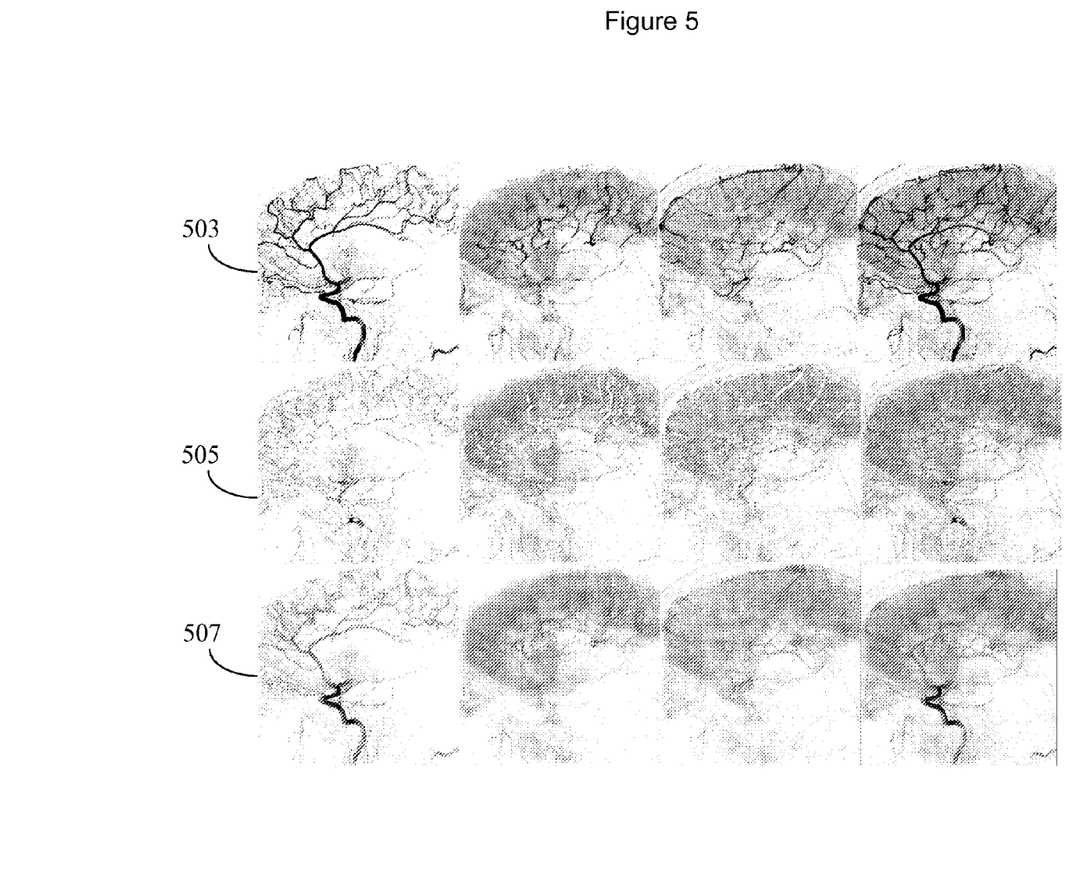
FIG. 5 shows known opacification images, images with vessels suppressed by a mask created from thresholding band-pass filtered image data images with vessels suppressed by a band-reject filter, according to invention principles.

FIG. 5 shows known opacification images in row 503, images with vessels suppressed by a mask created from thresholding band-pass filtered image data in row 505 and images with vessels suppressed by a band-reject filter in row 507. Four images are shown on each row. The images show opacification of a digital subtraction angiography (DSA) image sequence, with the rightmost image in each row being the opacified result of combining the other three images. Row 503 shows known opacification. Row 505 shows vessels suppressed by a mask created from thresholding a band-pass image. Row 507 shows images with the vessels suppressed by a band-reject filter. Both the thresholded band-pass mask produced images and the band-reject filter produced images result in opacified images showing parynchemal perfusion much more clearly with the vessels suppressed. An output image may additionally use a color map to identify the time at which the contrast at a particular pixel is at its peak.

Figure 6:
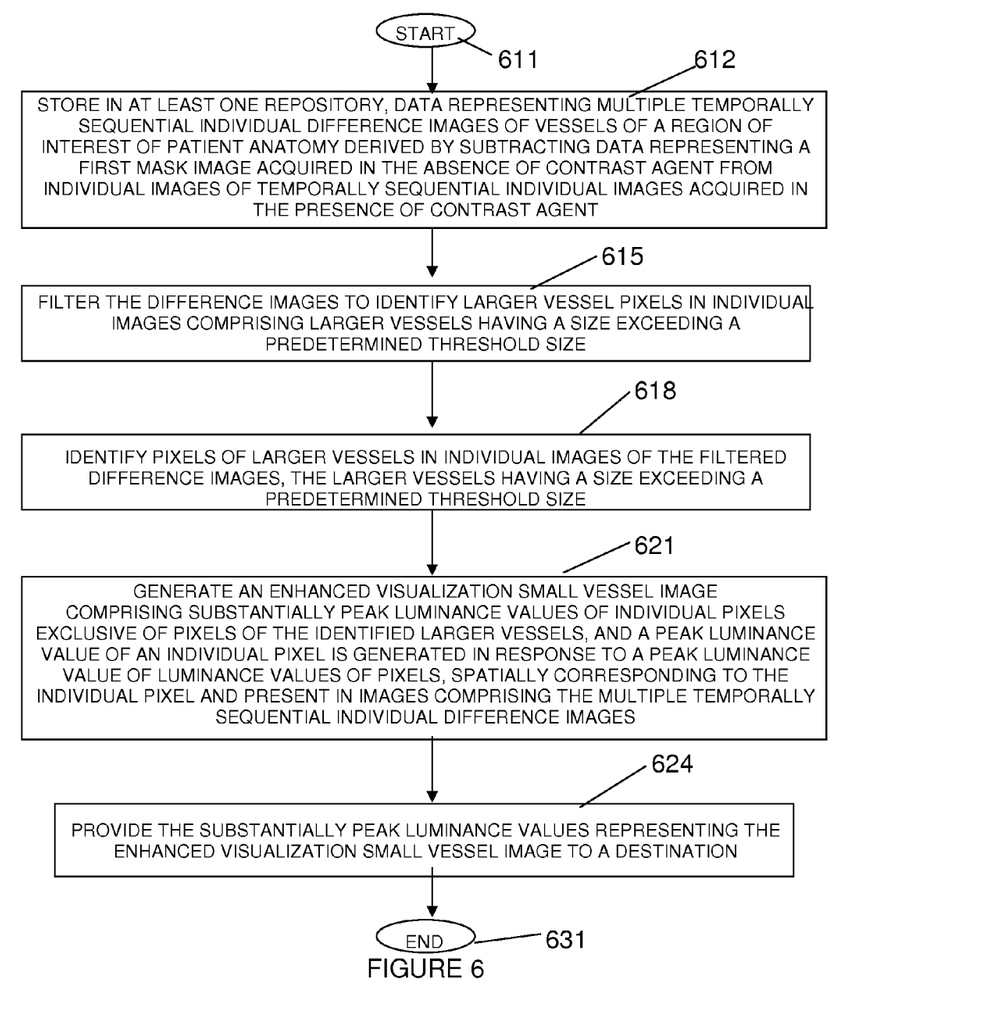
FIG. 6 shows a flowchart of a process employed by a system for generating medical image data representing smaller vessels including capillaries of a region of patient anatomy, according to invention principles.

FIG. 6 shows a flowchart of a process employed by system 10 (FIG. 1) for generating medical image data representing smaller vessels including capillaries of a region of patient anatomy. In step 612 following the start at step 611, processor 15 stores in at least one repository 17, data representing multiple temporally sequential individual difference images of vessels of a region of interest of patient anatomy derived by subtracting data representing a first mask image acquired in the absence of contrast agent from individual images of temporally sequential individual images acquired in the presence of contrast agent. Processor 15 subtracts data representing a first mask from the individual images to remove background image detail and emphasize vessel structure in providing the individual difference images. In step 615, image data processor 15 filters the difference images to identify larger vessel pixels in individual images comprising larger vessels having a size exceeding a predetermined threshold size. Processor 15 filters the difference images using at least one of, (a) a band-pass filter and (b) a band reject filter. Processor 15 in step 618, identifies pixels of larger vessels in individual images of the filtered difference images where the larger vessels have a size exceeding a predetermined threshold size such as a diameter substantially in the range 1-40 pixels. The system is configurable to filter out a wide variety of pixel range not just the 1-40 pixel range.

In step 621, processor 15 generates an enhanced visualization small vessel image comprising substantially peak luminance values of individual pixels exclusive of pixels of the identified larger vessels. A peak luminance value of an individual pixel is generated in response to a peak luminance value of luminance values of pixels, spatially corresponding to the individual pixel and present in images comprising the multiple temporally sequential individual difference images. A peak luminance value may comprise a minimum or maximum luminance value as luminance values are readily inverted. Processor 15 generates a peak luminance value of an individual pixel in response to selecting a peak luminance value of luminance values of pixels, spatially corresponding to the individual pixel and present in images comprising the multiple temporally sequential individual difference images. Processor 15 generates a cumulative image comprising cumulative luminance values of pixels excluding the identified larger vessel pixels. A cumulative luminance value of an individual pixel is generated from luminance values of pixels, spatially corresponding to the individual cumulative pixel and present in images comprising the multiple temporally sequential individual difference images. Output processor 27 in step 624 provides the substantially peak luminance values comprising cumulative luminance values representing the enhanced visualization small vessel cumulative image, to a destination. Image data processor 15 generates the cumulative luminance value of an individual pixel by at least one of, (a) adding the luminance values of pixels, (b) using a weighted sum of the luminance values of pixels and (c) interpolating between the luminance values of pixels. The process of FIG. 6 terminates at step 631.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block (s) of the flowchart(s). A user interface processor or generator is a known element comprising electronic circuitry or software or a combination of both for generating display elements or portions thereof. A user interface comprises one or more display elements enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display elements, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the elements for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display elements in response to signals received from the input devices. In this way, the user interacts with the display elements using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. A histogram of an image is a graph that plots the number of pixels (on the y-axis herein) in the image having a specific intensity value (on the x-axis herein) against the range of available intensity values. The resultant curve is useful in evaluating image content and can be used to process the image for improved display (e.g. enhancing contrast).

The system and processes of FIGS. 1-6 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system generates a maximally perfused image providing enhanced visualization of capillary (or parenchymal) perfusion in which individual image picture elements (pixels) represent peak (substantially maximally opacified) contrast agent at their respective image locations over the duration of contrast agent flow. Further, the processes and applications may, in alternative embodiments, be located on one or more (e.g., distributed) processing devices on a network linking the units FIG. 1. Any of the functions and steps provided in FIGS. 1-6 may be implemented in hardware, software or a combination of both. No claim element herein is to be construed under the provisions of 35 U.S.C. 112, sixth paragraph, unless the element is expressly recited using the phrase "means for."

What is claimed is:

1. A system for generating medical image data representing smaller vessels including capillaries of a region of patient anatomy, comprising:
at least one repository for storing data representing a plurality of temporally sequential individual difference images of vessels of a region of interest of patient anatomy derived by subtracting data representing a first mask image acquired in the absence of contrast agent from individual images of temporally sequential individual images acquired in the presence of contrast agent;
an image data processor for,
identifying pixels of larger vessels in individual images of said difference images, said larger vessels having a size exceeding a predetermined threshold size;
generating an enhanced visualization small vessel image comprising substantially peak luminance values of individual pixels exclusive of pixels of the identified larger vessels, and a peak luminance value of an individual pixel is generated in response to a peak luminance value of luminance values of pixels,
spatially corresponding to said individual pixel and present in images comprising said plurality of temporally sequential individual difference images; and
an output processor for providing said substantially peak luminance values representing said enhanced visualization small vessel image to a destination.

2. A system according to claim 1, wherein
said image data processor subtracts said data representing said first mask from said individual images to remove background image detail and emphasize vessel structure in providing said individual difference images and
said peak luminance comprise a maximum or minimum luminance.

3. A system according to claim 1, wherein
said image data processor filters said difference images to identify larger vessel pixels in individual images comprising larger vessels having a size exceeding a predetermined threshold size.

4. A system according to claim 3, wherein
said image data processor filters said difference images using at least one of, (a) a bandpass filter and (b) a band reject filter.

5. A system according to claim 1, wherein
said image data processor identifies pixels of larger vessels comprising vessels having a diameter substantially in the range 1-40 pixels.

6. A system according to claim 1, wherein
said image data processor generates a peak luminance value of an individual pixel in response to selecting a luminance value, indicating maximal opacification, of luminance values of pixels,
spatially corresponding to said individual pixel and present in images comprising said plurality of temporally sequential individual difference images.

7. A method according to claim 1, including the activity of generating a peak luminance value of an individual pixel in response to selecting a peak luminance value, indicating maximal opacification, of luminance values of pixels, spatially corresponding to said individual pixel and present in images comprising said plurality of temporally sequential individual difference images.

8. A system for generating medical image data representing smaller vessels including capillaries of a region of patient anatomy, comprising:
at least one repository for storing data representing a plurality of temporally sequential individual difference images of vessels of a region of interest of patient anatomy derived by subtracting data representing a first mask image acquired in the absence of contrast agent from individual images of temporally sequential individual images acquired in the presence of contrast agent;

an image data processor for, identifying pixels of larger vessels in individual images of said difference images, said larger vessels having a size exceeding a predetermined threshold size;

generating a cumulative image comprising cumulative luminance values of pixels excluding the identified larger vessel pixels, and a cumulative luminance value of an individual pixel is generated from luminance values of pixels, spatially corresponding to said individual cumulative pixel and present in images comprising said plurality of temporally sequential individual difference images; and an output processor for providing said cumulative luminance values representing said cumulative image to a destination.

9. A system according to claim 8, wherein
said image data processor generates said cumulative luminance value of an individual pixel by adding said luminance values of pixels.

10. A system according to claim 8, wherein
said image data processor derives said individual cumulative pixel luminance value by using a weighted sum of said luminance values of pixels.

11. A system according to claim 8, wherein
said image data processor derives said individual cumulative pixel luminance value by interpolating between said luminance values of pixels.

12. A method for generating medical image data representing smaller vessels including capillaries of a region of patient anatomy, comprising the activities of:

storing in at least one repository, data representing a plurality of temporally sequential individual difference images of vessels of a region of interest of patient anatomy derived by subtracting data representing a first mask image acquired in the absence of contrast agent from individual images of temporally sequential individual images acquired in the presence of contrast agent;

identifying pixels of larger vessels in individual images of said difference images, said larger vessels having a size exceeding a predetermined threshold size;

generating an enhanced visualization small vessel image comprising substantially peak luminance values of individual pixels exclusive of pixels of the identified larger vessels, and a peak luminance value of an individual pixel is generated in response to a peak luminance value of luminance values of pixels, spatially corresponding to said individual pixel and present in images comprising said plurality of temporally sequential individual difference images; and providing said substantially peak luminance values representing said enhanced visualization small vessel image to a destination.

13. A method according to claim 12, including the activity of subtracting said data representing said first mask from said individual images to remove background image detail and emphasize vessel structure in providing said individual difference images.

14. A method according to claim 12, including the activity of filtering said difference images to identify larger vessel pixels in individual images comprising larger vessels having a size exceeding a predetermined threshold size.

15. A method according to claim 14, wherein
said image data processor filters said difference images using at least one of, (a) a bandpass filter and (b) a band reject filter.

16. A method according to claim 12, including the activity of identifying pixels of larger vessels comprising vessels having a diameter substantially in the range 1-40 pixels.

* * * * *